(12) United States Patent
Knapp

(10) Patent No.: US 6,500,116 B1
(45) Date of Patent: Dec. 31, 2002

(54) SURGICAL RETRACTOR HAVING IMPROVED BLADES

(75) Inventor: Tracey Knapp, Lawrenceville, GA (US)

(73) Assignee: Genzyme Corporation, Cambridge, MA (US)

( * ) Notice: Subject to any disclaimer, the term of this patent is extended or adjusted under 35 U.S.C. 154(b) by 128 days.

(21) Appl. No.: 09/655,921

(22) Filed: Sep. 6, 2000

Related U.S. Application Data

(63) Continuation-in-part of application No. 09/345,859, filed on Jul. 1, 1999, now Pat. No. 6,348,036.
(60) Provisional application No. 60/117,333, filed on Jan. 24, 1999.

(51) Int. Cl.[7] .................................................. A61B 1/32
(52) U.S. Cl. ........................ 600/232; 600/231; 600/210; 600/213; 600/215
(58) Field of Search ................................ 600/201, 213, 600/214, 217, 231, 232, 233, 235, 210, 215, 219

(56) References Cited

U.S. PATENT DOCUMENTS

| 2,450,194 | A | * | 9/1948 | Glaser | |
|---|---|---|---|---|---|
| 5,730,757 | A | | 3/1998 | Benetti et al. | |
| 5,795,291 | A | * | 8/1998 | Koros et al. | 600/232 |
| 5,984,865 | A | * | 11/1999 | Farley et al. | 600/213 |
| 5,984,867 | A | * | 11/1999 | Deckman et al. | 600/232 |
| 6,042,540 | A | * | 3/2000 | Johnston et al. | 600/213 |
| 6,042,542 | A | * | 3/2000 | Koros et al. | 600/231 |
| 6,206,828 | B1 | * | 3/2001 | Wright | 600/232 |
| 6,348,036 | B1 | * | 2/2002 | Looney et al. | 600/232 |

FOREIGN PATENT DOCUMENTS

| DE | | 2951664 | | 7/1981 | |
|---|---|---|---|---|---|
| GB | | 2052998 | A * | 2/1981 | 600/232 |
| WO | WO | 00/42935 | | 7/2000 | |

* cited by examiner

Primary Examiner—Jeffrey A. Smith
(74) Attorney, Agent, or Firm—Richard D. Allison; Thomas J. DesRosier

(57) ABSTRACT

The present invention relates to surgical retractors having improved blades for use, on the retractor and devices for stabilizing a predetermined area of the body during a surgical procedure, more particularly to surgical retractors and stabilizing devices used in connection with minimally invasive coronary artery bypass grafting surgical procedures, and more specifically to surgical retractors and stabilizing devices especially configured for use with each other for such surgical procedures wherein the retractor includes a plurality of grooves on the bottom surface thereof and a plurality of blades having a member that is releasably received in the grooves and which also allows for the pivotal movement of the blades relative to the arms of the retractor and further including nesting blades having a third section which is generally linear and second sections which are preferably curved about 180 degrees to allow for the simplified insertion of the blades into the chest incision and the providing for the secure and stable positioning of the retractor relative to the chest of the patient.

19 Claims, 13 Drawing Sheets

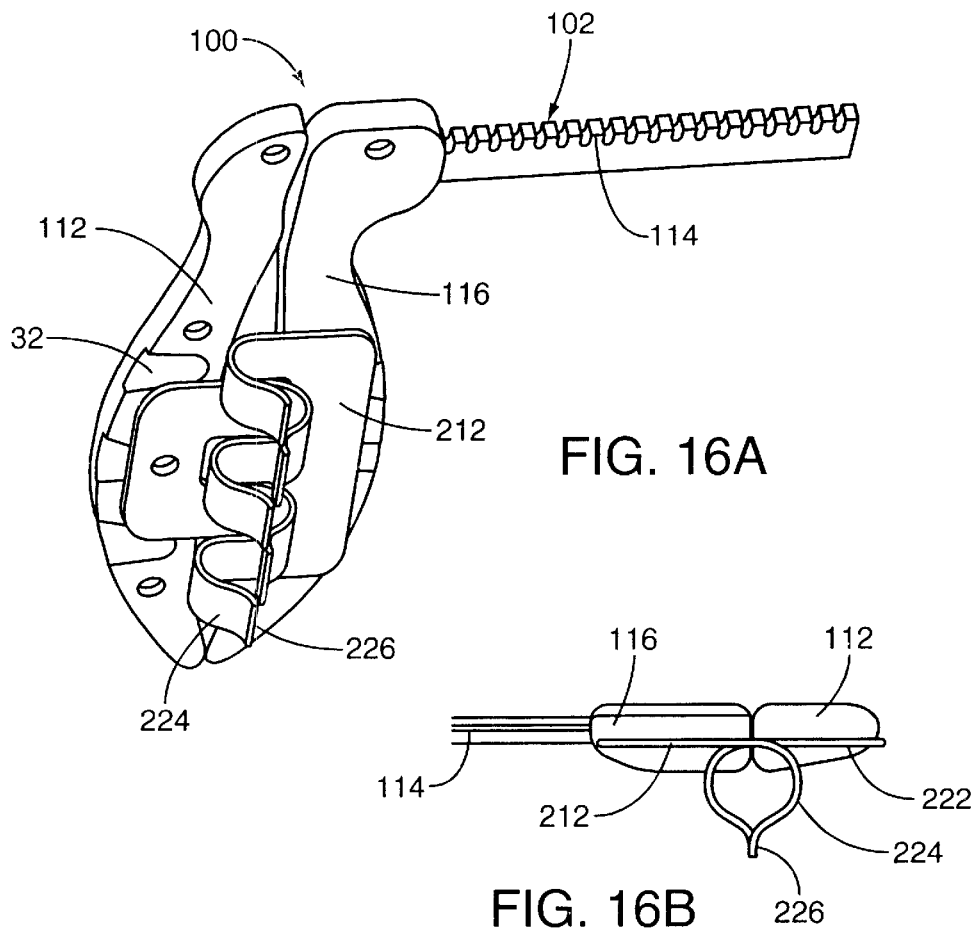
FIG. 16A
FIG. 16B
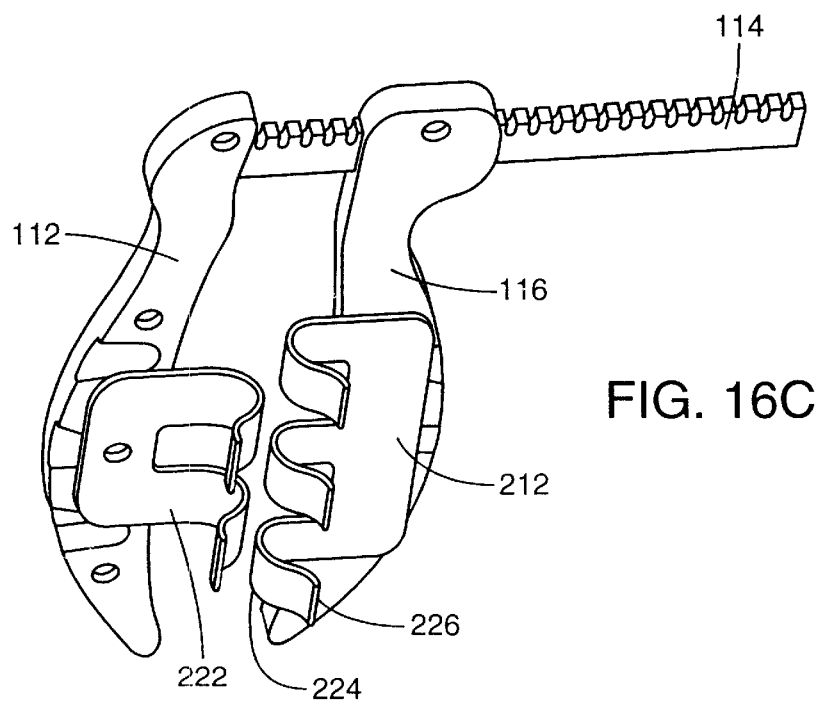
FIG. 16C

SURGICAL RETRACTOR HAVING IMPROVED BLADES

RELATED APPLICATION

The present application is a continuation-in-part of U.S. Ser. No. 09/345,859 filed on Jul. 1, 1999 U.S. Pat. No. 6,348,036 and U.S. Ser. No. 60/117,333 filed on Jan. 24, 1999, all of which are commonly assigned. The priority of each application is claimed hereby.

FIELD OF INVENTION

The present invention relates to surgical retractors and devices for stabilizing a predetermined area of the body during a surgical procedure, more particularly to surgical retractors and stabilizing devices used in connection with minimally invasive coronary artery bypass grafting surgical procedures, and more specifically to surgical retractors are stabilizing devices especially configured for use with each other for such surgical procedures.

BACKGROUND OF THE INVENTION

Diseases of the cardiovascular system affect million s of people each year and are a cause of death for large numbers of people in the United States and throughout the world. A particularly prevalent form of cardiovascular disease involves a reduction in the blood supply to the heart caused by atherosclerosis (coronary artery disease) or other conditions that create a restriction in blood flow at a critical point in the cardiovascular system leading to the heart.

One technique for treating such a blockage or restriction is a surgical procedure known as a coronary artery bypass graft procedure, which is more commonly known as "a heart bypass" operation. The surgical correction of occluded or stenosed coronary arteries by means of bypass grafting are probably still the most common procedures performed today, especially when multiple grafts are needed.

In the coronary artery bypass graft procedure, the surgeon either removes a portion of a vein from another part of the body for grafting or detaches one end of an artery and connects that end past the obstruction while leaving the other end attached to the arterial supply. When using a vein from another part of the body, the surgeon installs this portion at points that bypass the obstruction. In both cases, the objective is to restore normal blood flow to the heart.

In addition, when using this technique the surgeon makes a long incision down the middle of the chest, saws through the sternum, spreads the two halves of the sternum apart using either curved or straight blades. The curved blades are commonly known as "Cooley" style blades. The curved blades are preferred by many surgeons because they provide the surgeon with better stabilization of the retractor in the chest incision because the sternum is captured within the curvature of the blade. The problem with these types of blades is that they are more difficult to insert because they have a larger side profile. The other type of commonly used blades are the straight blades. These are generally known as "Finochietto" style blades. The straight blades are preferred by many surgeons because they have a low side profile and are easy to insert into the chest incision. The difficulty with the straight blades is that they offer the surgeon less stabilization of the retractor in the chest incision than the curved blades. Once the blades of the retractor are inserted, the surgeon may then perform the procedures necessary to connect the surgical patient to a cardiopulmonary bypass machine to continue the circulation of oxygenated blood to the rest of the body while the heart is stopped and the graft is being sewn in place although such a procedure is one common technique for treatment, the procedure is lengthy, traumatic, considerably expensive and can damage the heart, the central nervous system and the blood supply.

In recent years, and in an effort to reduce expense, risk and trauma to the patient, physicians have turned to less invasive surgical approaches to the heart, such as intercostal and endoscopic access to the surgical site. With such procedures, the heart is beating during the surgical procedure. Thus, there is no need for any form of cardiopulmonary bypass and there is no need to perform the extensive surgical procedures necessary to connect the patient to such a bypass machine.

Such attempts at performing minimally invasive bypass grafting on a beating heart, however, have been thought of as being tedious, dangerous and difficult because of the delicate nature of the surgical procedure, the lack of adequate access through a reduced surgical field, and the lack of a way to adequately stabilize and reduce tissue movement at the graft site. Because these procedures are performed while the heart muscle is continuing to beat, the blood continues to flow and the heart continues to move in three dimensional movement while the surgeon is attempting to sew the graft in place. Also, the surgical procedure to install the graft requires placing a series of sutures through an extremely small vessel and onto tissue that continues to move during the procedure. It is necessary that these sutures be fully and securely placed so the graft is firmly in position and does not leak.

There is disclosed in U.S. Pat. No. 5,730,757, an access platform for the dissection of an internal mammary artery. The described access platform has first and second blades interconnected to a spreader member that laterally drives the blades apart together and support pads interconnected to the first blade. A torsional member is operably interconnected to the first blade and the spreader member and is used to vertically displace the first blade in either direction. Thus, increasing the surgeon's working space and visual access for the dissection of the internal mammary artery. A tissue retractor interconnected to the blades is used to draw the soft tissue around the incision away from the surgeon's work area. It is further provided that the access platform can include a port that can be used to mount a heart stabilizer instrument. In U.S. Pat. No. 2,450,194 granted to Glaser, an adjustable retractor is disclosed. This retractor includes movable blade structures on each retractor arm wherein the blades include tubular sleeves that include a set screw to hold the blades in a fixed position relative to the retractor arms.

There also is described in U.S. Pat. No. 5,875,782 granted to Ferrari et al. and U.S. Pat. No. 5,894,843 granted to Benetti et al. an apparatus for stabilizing the predetermined area on a heart or other organ of a patient to enable a surgical procedure on a beating heart. The apparatus includes a bifircated member having two elongated prongs and an elongated handle. The handle segment can be movably attached to a rib retractor so that a person is not required to hold the handle segment. In one disclosed embodiment, the apparatus further includes a device to hold the bifurcated member in a position against the surface of the heart sufficiently so that a stabilizing force is applied against the heart and contraction of the heart does not cause either vertical or horizontal motion at the target site during the surgical procedure.

There also is described in U.S. Pat. No. 5,836,311 granted to Borst et al. an apparatus for stabilizing the predetermined area on a heart or other organ of a patient to enable a surgical procedure on a beating heart. The apparatus includes a single legged or bifurcated member having a plurality of suction members thereon which are attached to the surface of the heart using suction pressure. The arm portion of this device can be movably attached to a rib retractor or other surgical device so a person is not required to hold the handle segment and the suction device may be locked into position against the surface of the heart It is therefore desirable to provide a new system and devices related thereto for stabilizing a predetermined area of the body, such as the heart and methods related thereto. It is particularly desirable to provide such a system and devices thereto that are less complex and more user friendly in comparison to prior art devices. Such systems and devices thereto preferably are simple in construction and less costly than prior art devices.

SUMMARY OF THE INVENTION

The present invention features improved retractor blades for use on a surgical retractor and an improved system for retracting, stabilizing or manipulating a predetermined area of a body. The overall system includes a surgical retractor, a stabilization arm or apparatus and a tissue support or stabilization device, and methods of use related thereto. Also featured is a system that supports any of a number of surgical implements, for example a diaphragm retractor, a valve retractor, a light or suction device for use during a surgical procedure. The stabilization system and related devices and apparatuses thereto that are featured herein are particularly advantageous for use in performing off-pump coronary artery bypass grafting procedures in which the heart remains beating during the surgical procedure or in valve replacement procedures.

One advantage of the present invention relates to the use of the improved blades to provide blades that may be nested together and are easier to insert into the chest incision of the patient while providing stable retention of the sternum of the patient during the procedure.

A further advantage of the present invention relates to the use of the improved blades that are preferably pivotal relative to the retractor arms provide blades that are easier to insert into the chest incision of the patient while providing stable retention of the sternum of the patient during the procedure.

A further advantage of the present invention relates to the use of the external rail system on the arms of the retractor and even more preferably also on the rack segment of the retractor. The use of the external rail systems allows the stabilization arm to be attached to the retractor at any desired location and does not require that the stabilization arm be slid on from an end of an arm or specially attached in certain specific locations. Additionally, the sled of the present invention allows for a full range of motion which is controlled by a single knob that is easily manipulated by the surgeon.

The present invention features a surgical retractor including two arms, a rack segment and a plurality of sternal blades with at least one blade extending downwardly from each arm. Each blade includes an upper section adjacent to the bottom surface of the arm and a lower section extending distally of the arm. A slot on the bottom surface of the arms includes a tapered surface adjacent to the front edge thereof to facilitate the placement of the blades on the arms. A lip surface is also located adjacent to the slots on the bottom surface of the arms to securely retain the blades on the bottom surface of the arms during the procedure while still allowing the blades to be easily removable for initial positioning and subsequent sterilization following the procedure.

In a further embodiment of the present invention, the blades are configured with a straight surface along the bottom portion and a curved surface along the upper portion to allow the blades to be aligned during the initial insertion step while also capturing the tissue adjacent to the sternum of the patient with the curved portion once the blades are fully inserted into the chest incision.

In a general aspect, the stabilization system of the present invention is preferably used for stabilizing a predetermined area of a patient. This system preferably includes a retractor, a stabilization device for locally stabilizing the predetermined area and a stabilization arm that functionally secures the stabilization device to the retractor. The retractor preferably includes a rail system having two arms and a rack segment. The rack segment interconnects the two arms, for selectively spacing the two arms from each other and for maintaining the two arms in a desired fixed relationship. In a preferred form of the present invention, the two arms and rack segment are configured to receive the connector of the stabilization arm at the desired location thereon.

The stabilization device preferably includes a device of the type commonly known as the Cohn Cardiac Stabilizer marketed by the Genzyme Corporation of Cambridge Massachusetts, although horseshoe or suction type devices may also be used. The preferred form of the stabilization device is a generally square or rectangularly shaped member having a planar surface with centrally located opening therein. This opening is the area through which the surgeon performs the anastomosis or other procedure on the tissue of the beating heart. The stabilization device is preferably a two piece member so that once the anastomosis is completed, the pieces may be separated to remove the device from around the anastomosis. As described more fully below, flexible tapes are sutured through the tissue and then threaded through the stabilizing device. Once the stabilization device is positioned in the desired orientation and location in contact with the tissue, the flexible tapes are then pulled snug through the opening of the stabilization device to provide a system which minimizes the overall movement of the predetermined area of the tissue.

The stabilization arm preferably includes an elongated handle having a first end and a connector thereon for releasably connecting the stabilization device to the elongated handle first end. This connection allows the stabilization device to be pivotally and slidably moved to a desired position into contact with the predetermined area of the tissue of the patient. The stabilization arm also includes a mounting mechanism or sled member which is preferably slidable along the handle segment for removably securing the stabilization arm to at least one of the rails on the retractor arms and/or the rack segment of the retractor.

According to another aspect of the present invention, the arms of the retractor are configured with a front edge and a step in the top surface thereof to form an elongated rail surface along substantially the entire length thereof. The step is preferably spaced apart a predetermined and consistent distance from the front edge and is also located on the interconnecting or rack segment of the retractor. Also, the stabilization arm preferably includes a mounting mechanism or sled member which is configured to removably engage the front edge and the step at any desired location on one or more of the arms or the rack segment of the retractor. The mounting mechanism includes a lever for selectively engaging the step and front edge on the arm or rack segment of the retractor so the mounting mechanism is removably and slidably secured to the arms or the rack segment.

In yet another aspect of the present invention there is featured a sled member or mounting mechanism that allows the user to retain the stabilization arm in a sliding and fixed relationship relative to the retractor and patient while also allowing for the rotation of the sled member with respect to the retractor by manipulating a single knob. Furthermore, a lever on a bottom section of the sled member allows the sled member to be slidably and fixedly positioned along the arms and rack segment of the retractor. Each of these features enables the user to determine the optimum position for the stabilization arm and stabilization device while ensuring that the surgeon's view of the operative area is not unnecessarily obstructed. Additionally, these features allow the present invention to be used in many different medical procedures because of the versatility of system set up and orientation of the components of this invention.

Other aspects and embodiments of the invention are more fully discussed below.

BRIEF DESCRIPTION OF THE DRAWINGS

For a fuller understanding of the nature and desired objects of the present invention, reference is made to the following detailed description taken in conjunction with the accompanying drawing figures wherein like reference numbers denote corresponding parts throughout the several views and wherein:

FIGS. 16A, 16B and 16C bottom and side perspective views of the alternate form of the blade members attach d to the surgical retractor with the surgical retractor in the closed and open positions.

DESCRIPTION OF THE PREFERRED EMBODIMENT

Figure 1:
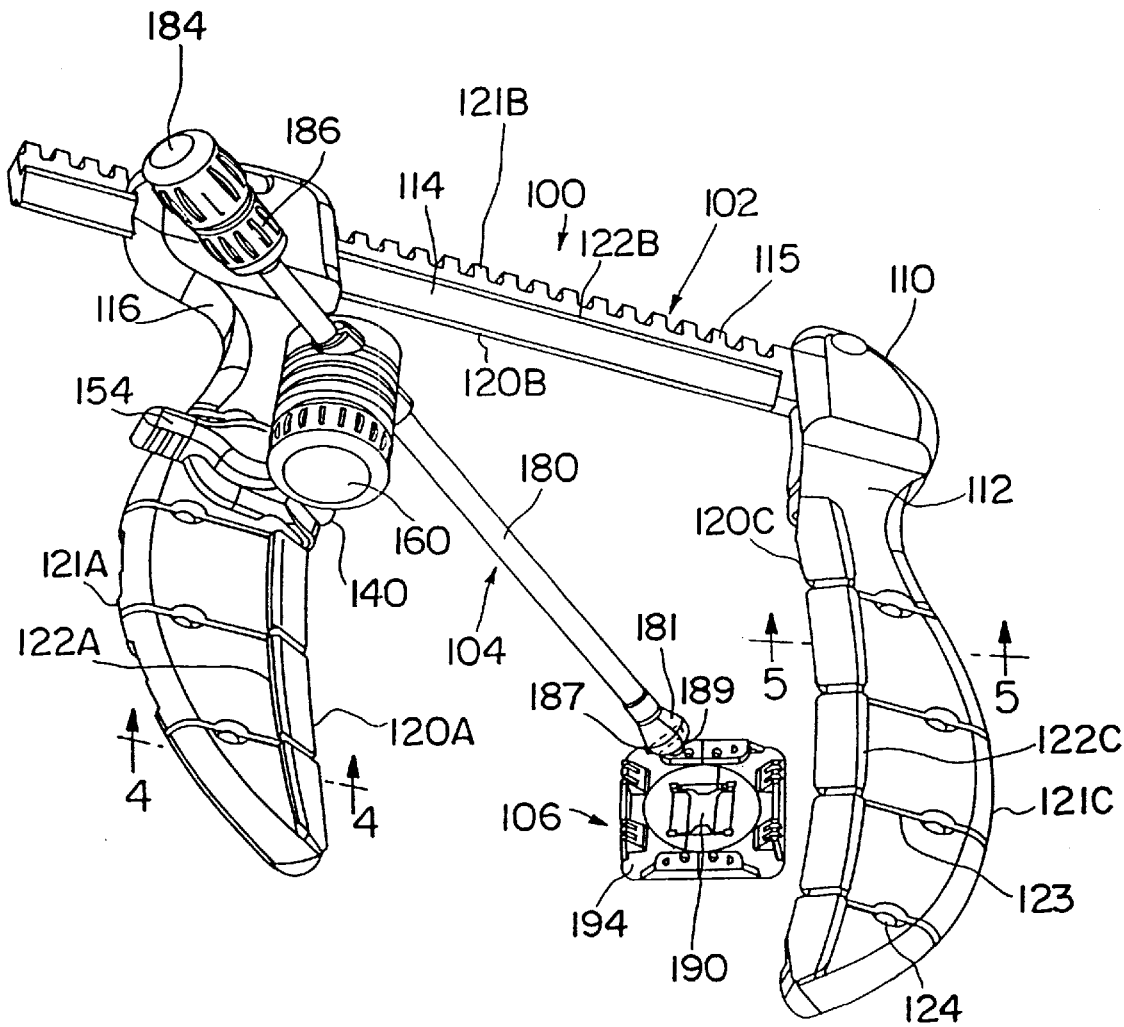
FIG. 1 is a perspective view of a stabilization system that assists in the stabilization of a predetermined area of a body according to a first aspect of the present invention with the handle removed for clarity.
Figure 2:
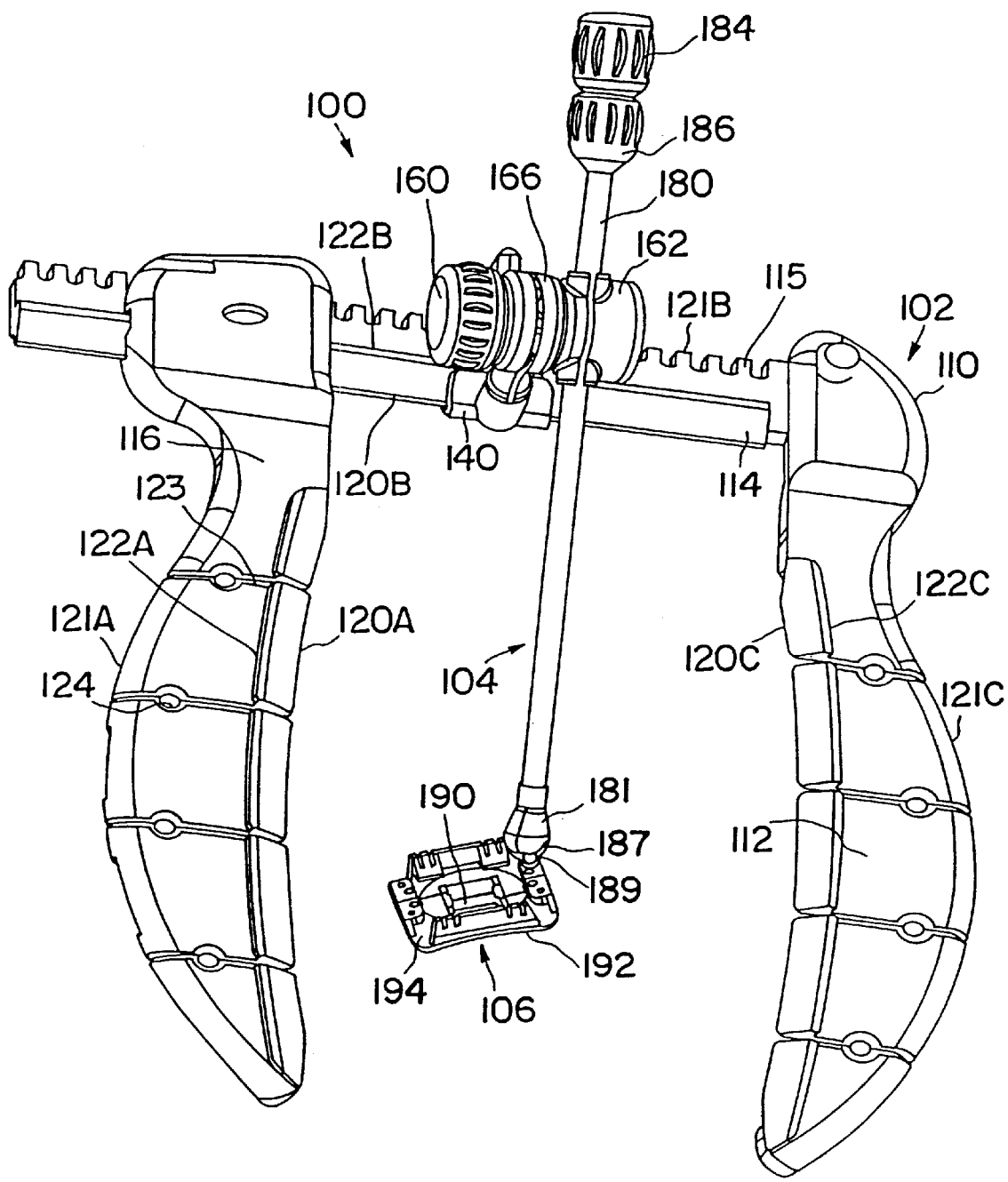
FIG. 2 is a perspective view of the stabilization system of the present invention with the handle removed for clarity and wherein the sled member is positioned on a rack segment of the retractor.
Figure 3A:
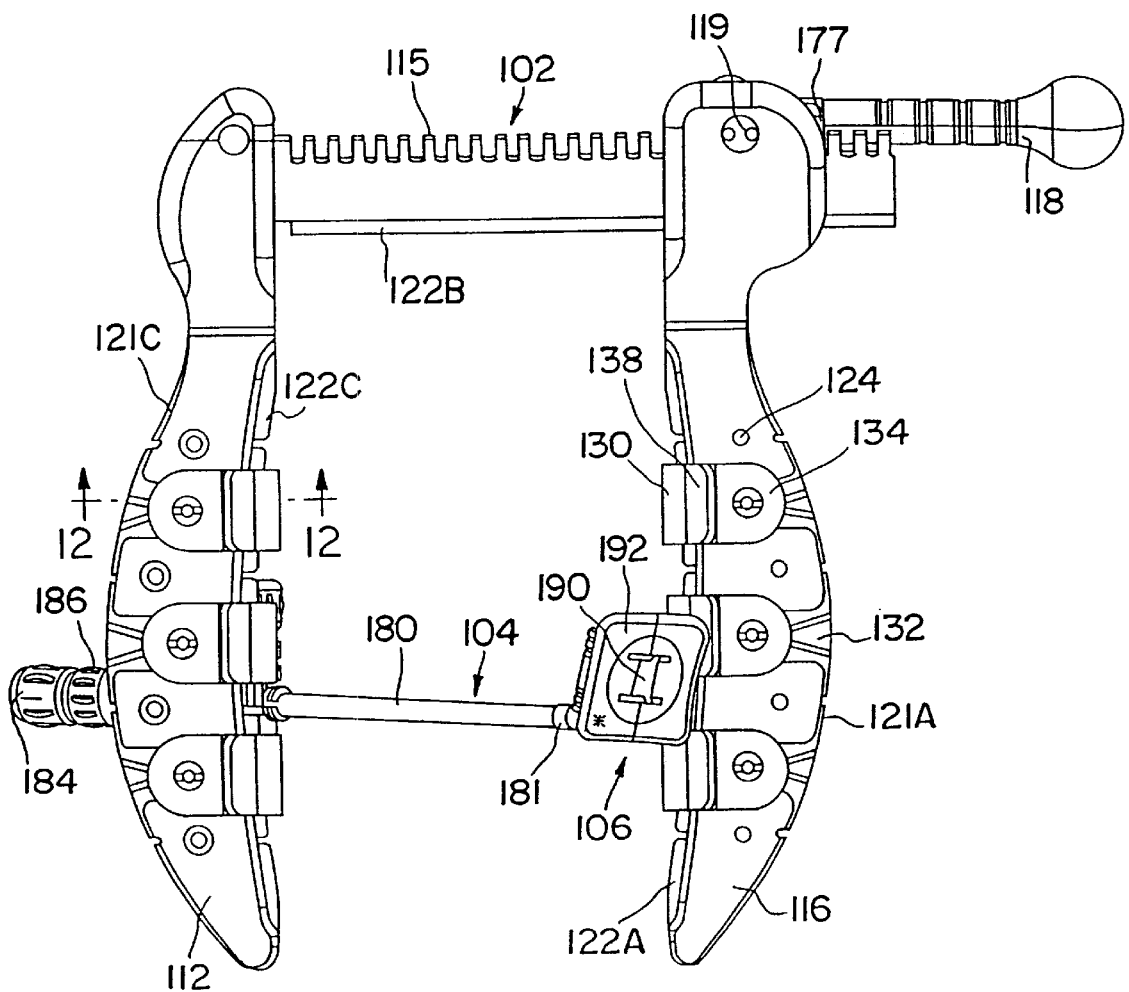
FIGS. 3A and 3B are bottom perspective and bottom isometric views of the stabilization system of FIG. 1.
Figure 3B:
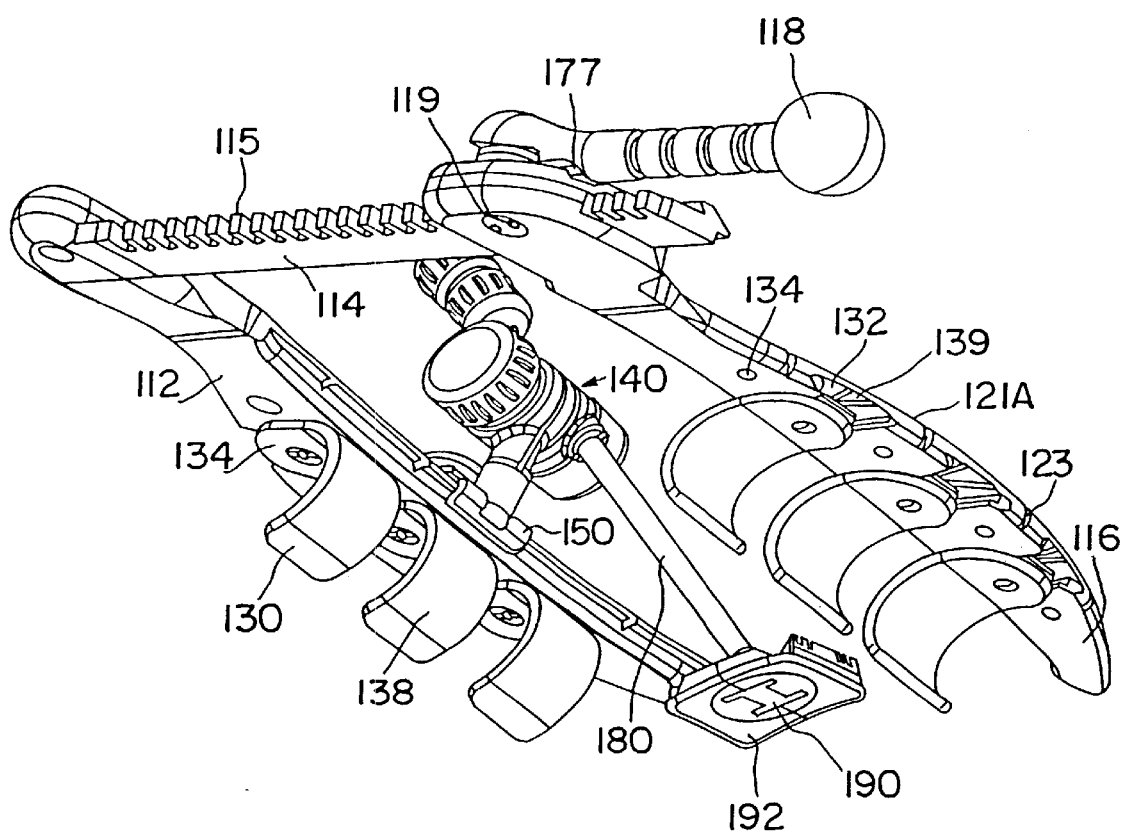
Figure 4:
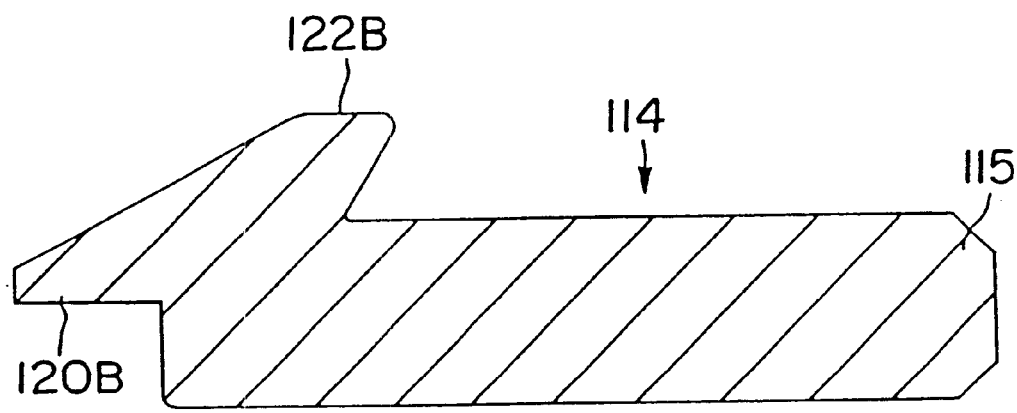
FIG. 4 is a cross sectional view of the rack segment taken generally along lines 4—4 of FIG. 1.
Figure 5:
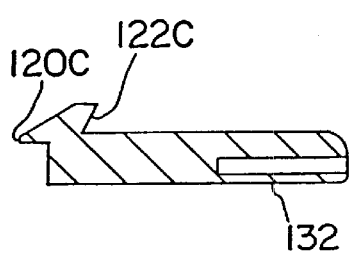
FIG. 5 is a cross sectional view of the arm section taken generally along lines 5—5 of FIG. 1.
Figure 7:
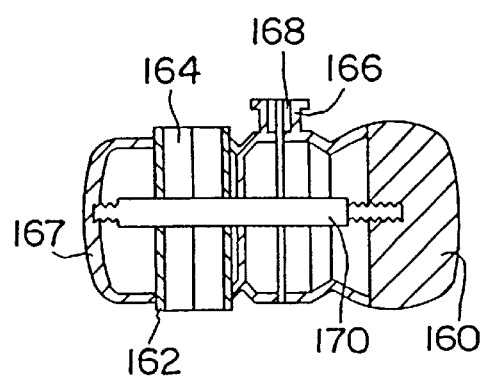
FIG. 7 is a cross-sectional view of the upper section of the sled member of the stabilization an of the present invention taken generally along lines 7—7 of FIG. 6A.
Figure 8:
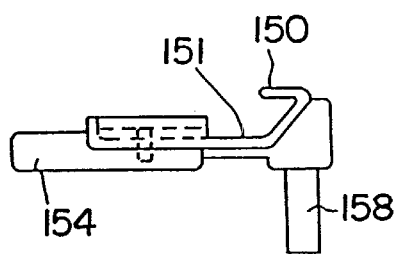
FIG. 8 is a side view of the bottom section of the sled member of the stabilization arm of the present invention.
Figure 9:
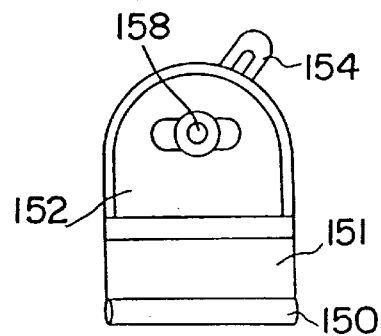
FIG. 9 is a bottom view of the bottom section of the sled member of the stabilization arm of the present invention.
Figure 6A:
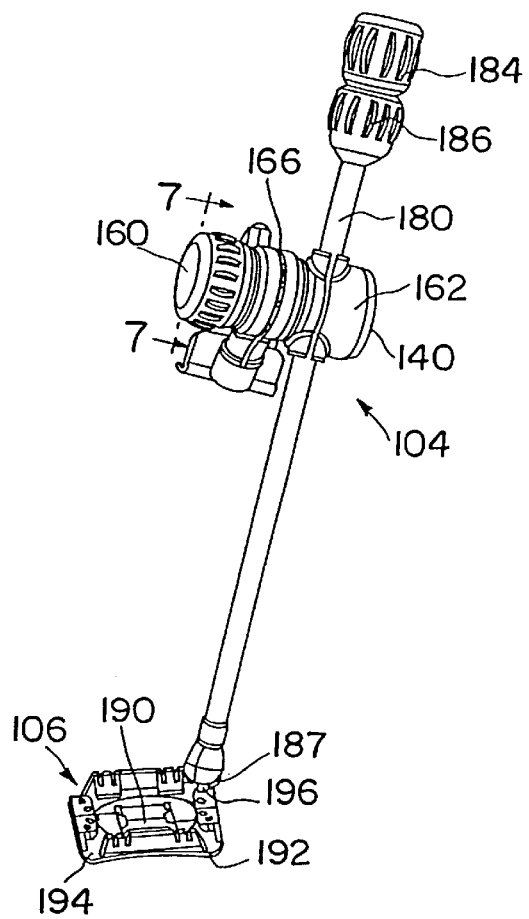
FIGS. 6A, 6B and 6C various elevational views of the stabilization arm and stabilization device of the present invention.
Figure 6B:
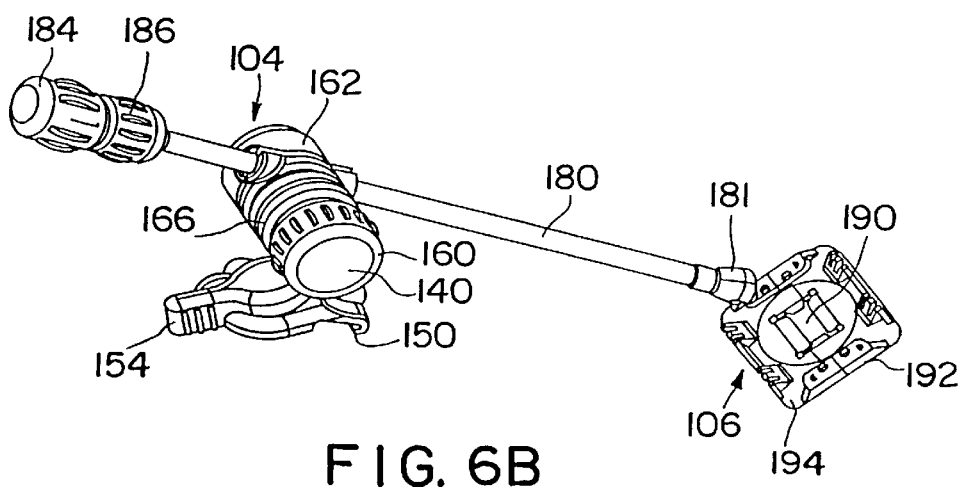
Figure 6C:
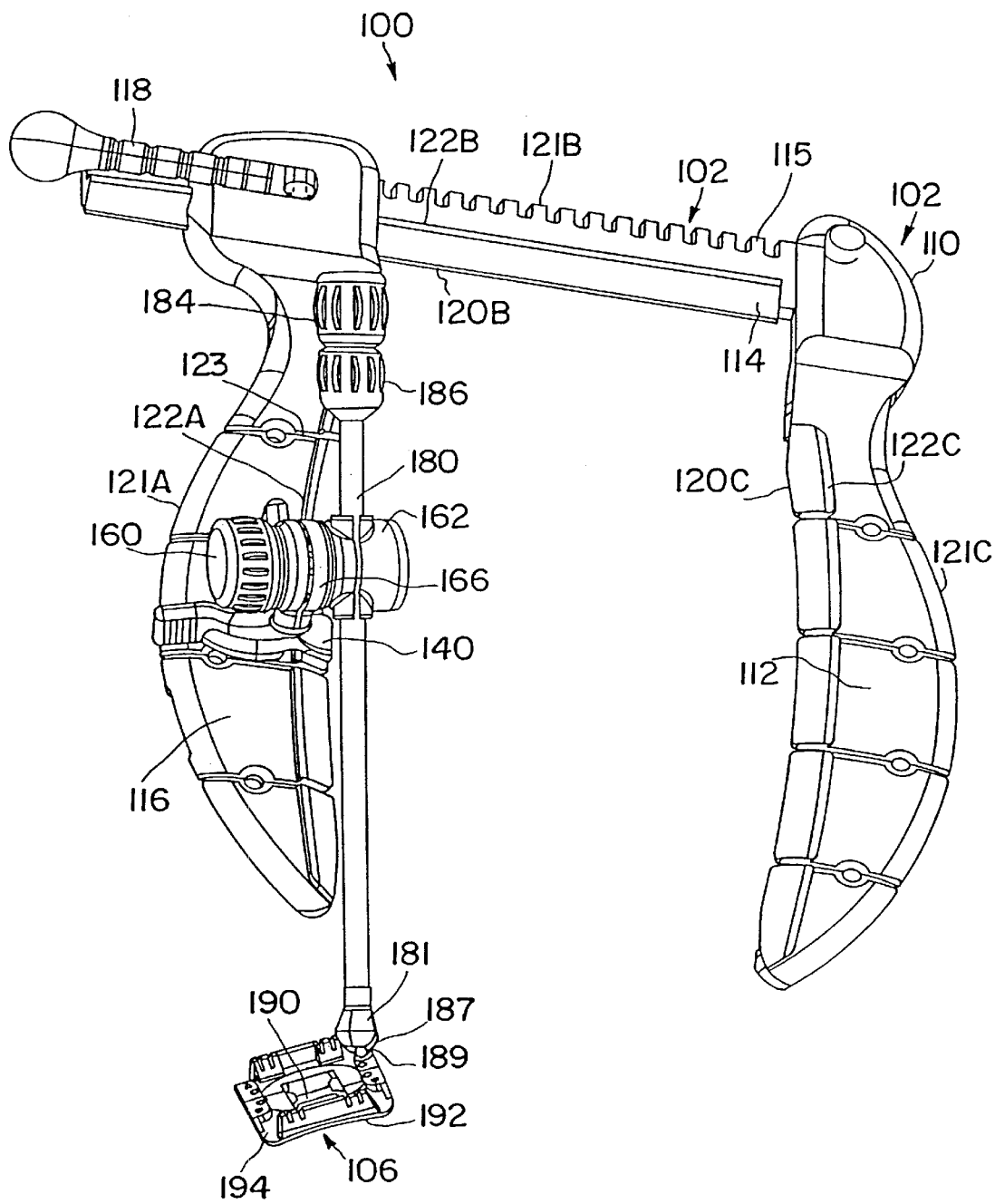
Figure 10:
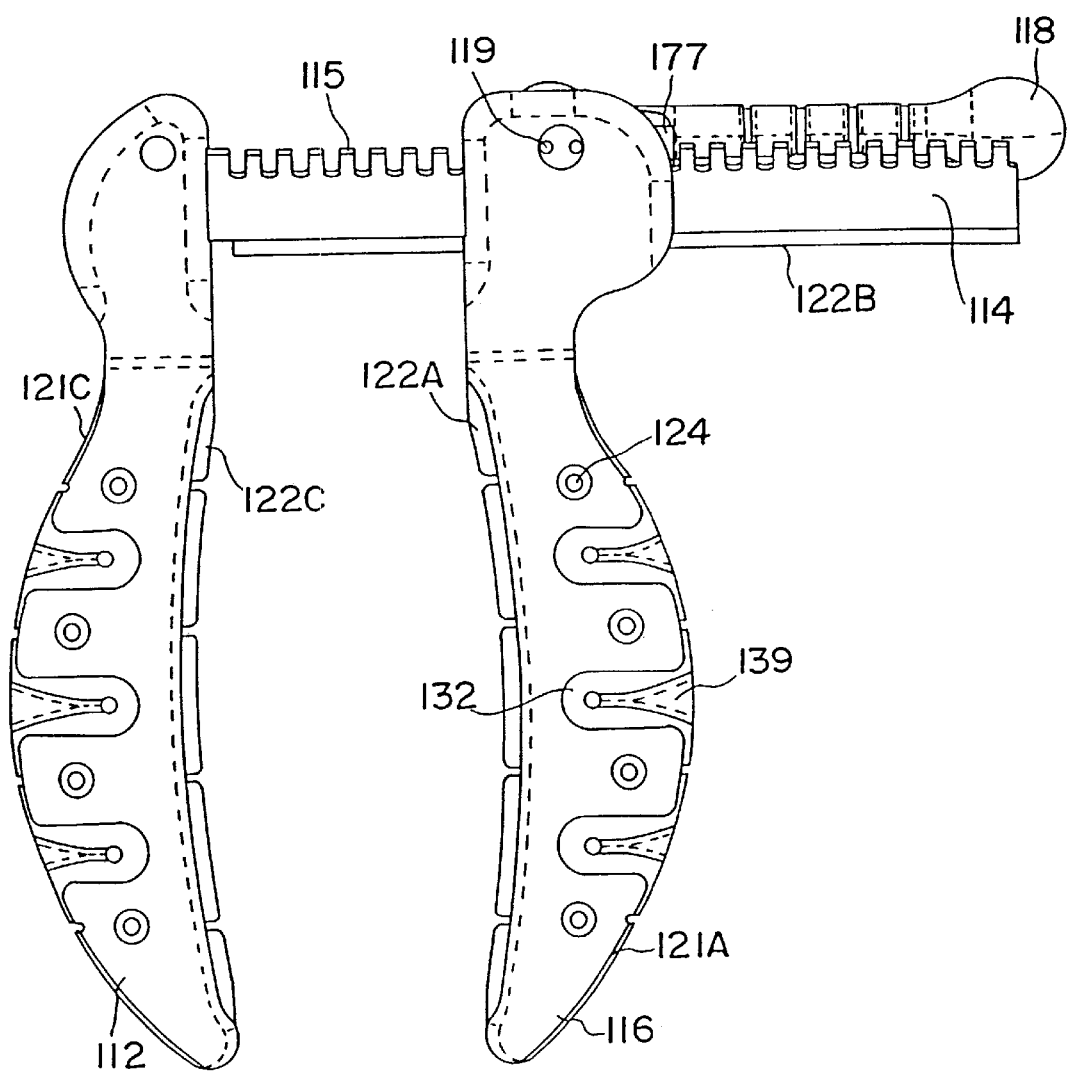
FIG. 10 bottom view of the retractor of the present invention with the blades removed.
Figure 11:
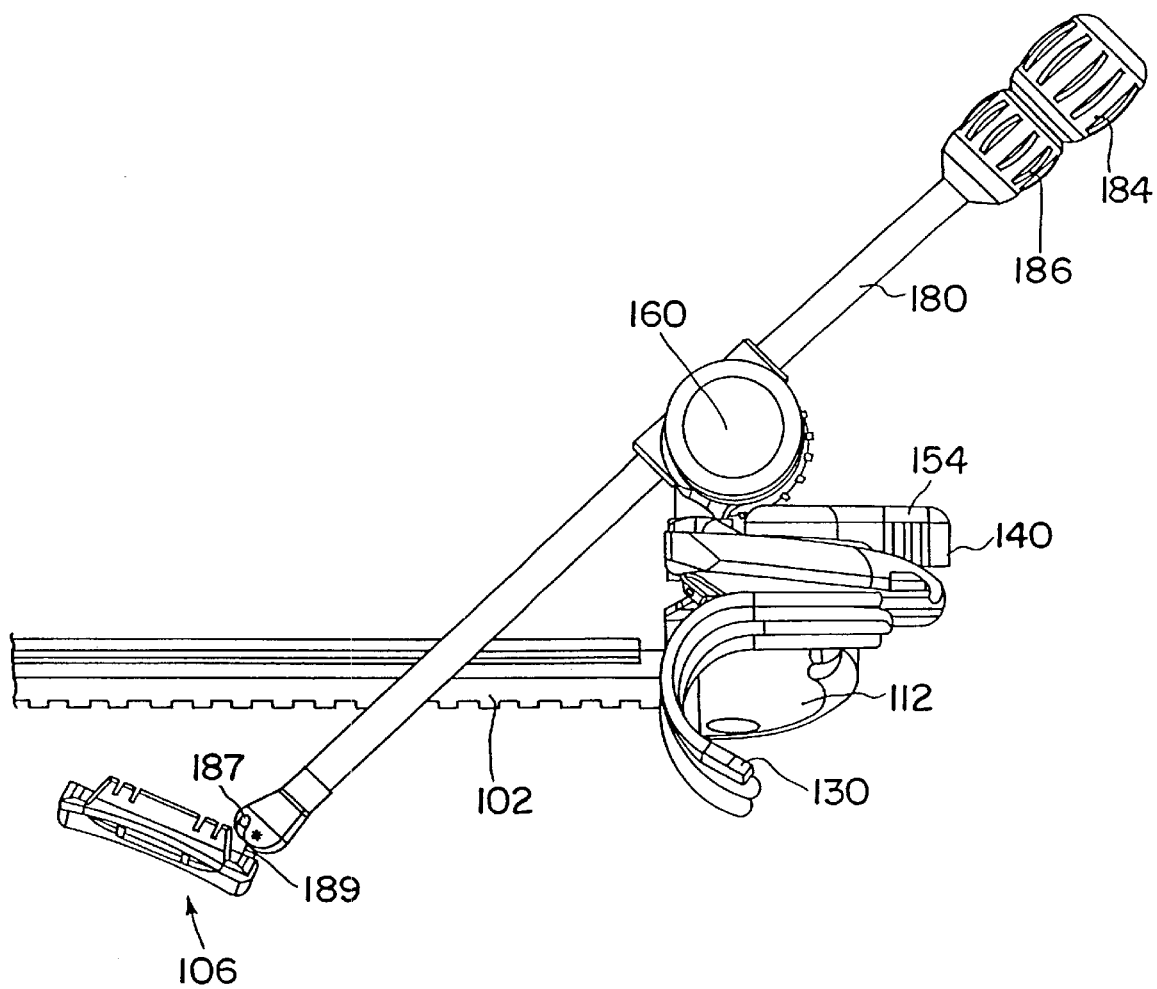
FIG. 11 is an end view of the retractor of the present invention with the blades thereon.
Figure 12:
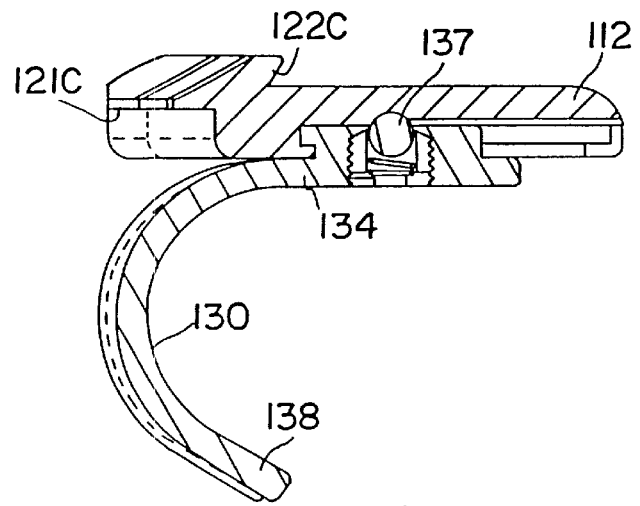
FIG. 12 is a cross sectional view taken generally along lines 12–12 of FIG. 3 with the blade inserted in the ridged slot of the arm.
Figure 13A:
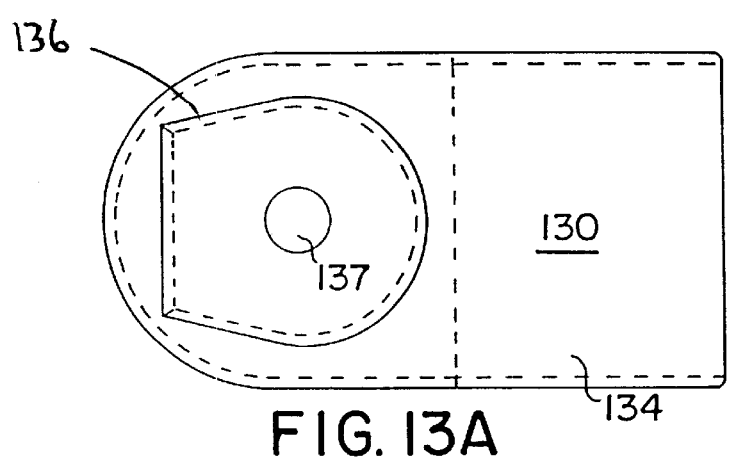
FIGS. 13A and 13B is a top and bottom perspective views of the blade member of the present invention.
Figure 13B:
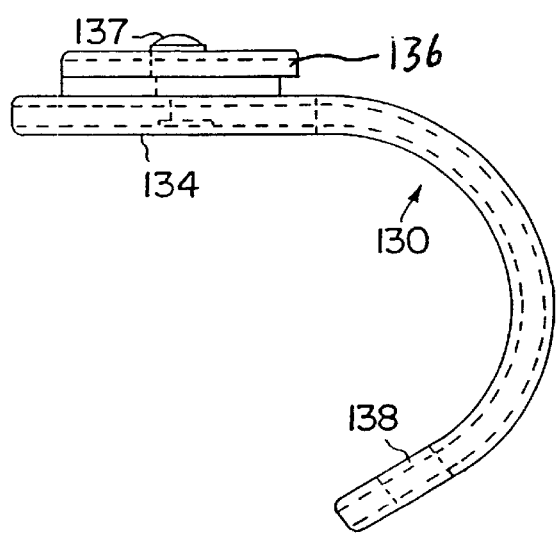

Referring now to the various figures of the drawings wherein like reference characters refer to like elements, there is shown various views of a preferred and alternate form of a stabilization system 100 according to the present invention for contributing to the stabilization of a predetermined area of a body such as the predetermined area of a heart or other organ of a patient to enable the physician to perform a surgical operation or procedure on a patient. The stabilization system 100 is particularly useful in connection with single or multiple vessel off-pump coronary artery bypass surgery on a beating heart through a sternotomy or mini-sternotomy incision.

A surgeon may use the stabilization system 100 to apply a slight contacting or compressive force on the heart in the area where the surgical procedure will occur so the heart's movement at that specific area is diminished. In a preferred form of this invention, the stabilization system 100 is used in combination with flexible tapes or sutures or other mechanical means so that the surface of the heart is stabilized using a combination of restraining and stabilizing forces. In certain procedures, it may also be advantageous to place a traction suture around an artery using a needle and suture thread to occlude the blood vessel. These sutures may then be attached to the stabilizing device so that the flow of blood through the blood vessel is selectively restricted.

Systems for stabilizing the heart of a patient are particularly useful for various heart suturing techniques or procedures. One example of this type of procedure is the performance of an anastomosis for a bypass graft. In this type of procedure, the physician is attempting to suture the circumference of a blood vessel that may be about 1 mm to a moving blood vessel on the surface of the heart. Another area of use of the present invention may be in brain surgery, heart valve surgery or other types of blood vessel surgery where stability is critically important to avoid disastrous consequences or where it is desirable to have a precisely defined and stable surgical field. One skilled in the art will appreciate that the present invention, although advantageously suited for heart surgery, can be used at any location on or within the body where tissue stabilization or isolation of a predetermined area is desired. This includes, but is not limited to, the liver, kidneys, bladder, stomach, intestines, brain and vascular and other soft tissue surgery. Additionally, one skilled in the art will appreciate, as hereinafter described, that the supporting components of the system can be adapted so that any surgical instrument or device can be self-supported during a surgical procedure.

Referring specifically to FIGS. 1–4, the stabilization system 100 according to the present invention includes a retractor 102, a stabilization sub-system or stabilization arm 104 and a stabilization device 106. The retractor 102 is specifically configured so the stabilization arm 104 can be secured thereto. The retractor 102, preferably includes a rigid L-shaped member 110 having an arm segment 112 and a rack segment 114. The retractor 102 also includes a movable second arm segment 116 having a handle 118 thereon which is movably associated with the L-shaped member 110.

The stabilization arm or sub-system 104 preferably includes an elongate handle segment 180 that preferably interconnects the retractor 102 and the stabilization device 106. The handle segment 180 preferably includes a first end having a distal connector 181 thereon to pivotally and removably retain the stabilization device 106 thereon. The handle segment 180 is attachable to the retractor 102 by a connector such as a mounting mechanism or sled member 140. The proximal or second end of the handle segment 180 preferably includes a knob 184 thereon that is rotatable with respect to the handle segment 180 to allow the movement of the stabilization device 106 to be pivotal and/or fixed with respect to the handle segment 180 by manipulating the knob 184 on the proximal end of the handle segment 180. This arrangement also allows the stabilization device 106 to be mountable on and removable from the distal connector 181.

The preferred form of the stabilization device 106 is generally a rectangular shape having an opening or window area 190 therein. The stabilization device 106 preferably includes a first surface 192 that is generally planar and may include a textured surface thereon to facilitate the engagement between the stabilization device and the tissue of the predetermined area or the heart of the patient. The second surface 194 of the stabilization device 106 preferably includes a post member 196 extending therefrom. The post member 196 is preferably releasably and rotatably engaged by the distal connector 181 on the first end of the handle segment 180.

As described briefly above, the retractor 102 preferably includes a handle 118 located on the second arm segment 116 and the handle 118 is rotatable for displacing the two arm segments 112,116 with respect to each other. In the preferred form of this invention, rotation of the handle 118 causes a pair of posts or pinions 119 to sequentially engage the teeth 115 located on the outer edge 121b of the rack segment 114 to increase or decrease the distance between the first and second arms 112 and 116. As shown, the handle includes a projection 177 on the bottom surface thereof which fits in a slot located in the retractor adjacent to the arm and rack segment to allow the user to lock the handle into position once the arms are in the desired position. This feature is particularly useful where the retractor is reused for a relatively long period of time for multiple procedures because the pinions and teeth on the retractor will gradually wear due to the pressure from the chest of the patient. As the wear occurs, the pressure from the sternum may cause the arms to move towards each other unless the arms or handle are retained in a locked position. In a specific illustrative embodiment, the rack segment 114 is configured with a finochetti type of rack as is known to those skilled in the art. In conjunction with the handle 118, the rack segment 114 and movable second arm 116 form a rack and pinion type of means for displacing the arm segments 112, 116 with respect to each other. As shown, this type of rack segment 114 includes a plurality of laterally extending teeth members 115 that engage the posts 119 or similar tooth engaging members located in operative contact with the handle 118 of the second arm segment 116. It is anticipated that a variety of mechanisms may be used to move the second arm segment 116 along the rack segment 114. For example, a gear mechanism, a slide and locking mechanism or similar arrangement may be used to accomplish the separation and fixation of the second arm 116 with respect to the first arm 112. It is within the scope of the present invention, however, for the retractor 102 to be configured or designed with any of a number of means known to those skilled in the art for selectively displacing the first and second arm segments, 112 and 116 either towards or away from each other in a parallel, obtuse or acute angled manner.

At least one arm segment and preferably each arm segment, 112 and 116 respectively, and the rack segment 114 are configured so as to each have a front edge surface 120a, 120b and 120c extending along the inner surface of each element of the retractor 102 such that the front edges of each of the arms and the rack segment face each other. The retractor 102 also preferably includes an outer edge surface 121a, 121b and 121c extending along the outer surface of the first and second arms, 112 and 116 respectively, of the retractor 102. A step surface 122a, 122b and 122c extends along the top surface of the first and second arms, 112 and 116 respectively, and the rack segment 114 in a spaced apart relationship with respect to the front edges of each of the surfaces of the first and second arms and the rack segment to form an elongate lip or external rail surface on the arms and rack segment of the retractor. The step surface 122a–c is preferably located a preset distance back from the front edge and forms an acute angle facing away from the front edge thereof on each of the arms and the rack segment. As described hereinafter, the front edge surfaces 120a–c and the step surfaces 122a–c on the top surface of the arms and rack segment are particularly arranged and configured to face each other and so that the mounting mechanism or sled member 140 can be readily secured to the retractor 102 by engaging the front edge surface (120a, 120b or 120c) and the associated step surface (122a, 122b or 122c) on each of the first and second arms, 112 and 116, and the rack segment 114.

As also shown in the top views of the preferred form of the present invention, the front edge surfaces 120a and 120c of the first and second arm segments that are adjacent to the step surfaces 122a and 122c are of a preferably slightly concave orientation such that the mid point of the first and second arms are spaced apart from each other a greater distance than the distance of either or both of the inner or outer ends of the first and second arms, 112 and 116. Additionally, the outer edge surfaces 121a and 121c of each arm preferably has a greater curvature than the front edge surfaces 120a and 120c of the same arm so that as the retractor 102 spreads the chest of the patient, the motion of separating the first and second arms, 112 and 116, is emphasized to increase the amount the chest of the patient is spread. Therefore, at a given distance of separation between the first and second arms, 112 and 116, the midpoints of the outer surface of the arms will be separated a further distance than at the ends adjacent to the rack segment or at the ends furthest from the rack segment 114 due to the overall generally clam shell shaped configuration of the preferred form of the present invention. An advantage of this configuration is that the surgeon is provided with an opening in the sternum of the patient that is wider in the center than along the edges so that the most common area of work for the surgeon is larger than a conventional retractor for the same amount of separation.

Additionally, as shown in the drawings, the top surface of each of the arms, 112 and 116, preferably include a plurality of slots 123 extending generally perpendicular to the lengthwise dimension of each arm. These slots 123 extend from the front edge surfaces 120a and 120c; through the step surfaces 122a and 122c; and to the outer edge surfaces 121a and 121c, respectively on each of the first and second arms, 112 and 116. These slots 123 are configured to extend through the front edge surface 120a and 120c of each arm, 112 and 116, to allow the sled member 140 to be moved therealong while not cutting or interfering with any sutures that may be positioned in the slots. Additionally, each of the slots 123 preferably include a through hole 124 in communication with the slot and extending through the arm. In the preferred use of the present invention, the slots 123 are preferably used to position sutures that have been threaded through the pericardium of the patient therein so that the pericardium or other tissue is retracted and held out of the line of sight of the surgeon by the sutures to better expose the heart of the patient. With the preferred form of the present invention, the sutures and clamps are retained out of the working area of the surgeon. The portion of the through hole 124 adjacent to the top and bottom surfaces of the arm are preferably tapered so that distal end of the clamps or other instruments that are used to hold the sutures may be placed and retained therein during the procedure. By allowing the distal ends of the instruments to be placed into the through holes 124, the sutures are held in a secure position during the procedure and may be adjusted as needed at any time by lifting the instrument and then reclamping the suture or releasing the clamp and then pulling the suture through the clamp and subsequently closing the clamp while it remains in the through hold. Additionally, it is anticipated that some surgeons may use these through holes to suture the retractor to the patient to minimize possible extraneous movement of the retractor during the procedure.

In an exemplary embodiment of the present invention, the bottom surface of each of the first and second arms, 112 and 116, on the retractor 102 include removable sternal blades 130 attached thereto. Each blade 130 is removable so as to facilitate the use of the retractor in a full or mini-sternotomy procedure by allowing for the selective positioning and spacing of the blades 130 as desired for the particular procedure as well as for resterilization of the retractor 102 and blades 130. As illustrated, the blades 130 are positioned along the bottom surface of the arms 112 and 116 and are preferably pivotal in the horizontal and vertical directions with respect to the arms. In a preferred form of the present invention, the blades 130 are pivotal in the horizontal direction of about thirty degrees and are slightly pivotal in the vertical direction. The blades 130 are slidable into elongate ridged slots 132 on the bottom surface of the first and second arms, 112 and 116. The blades 130 may swivel a limited distance and are selectively positioned in the slots 132 so as to evenly distribute the retraction forces or pressure along the contour of the sternum of the patient. An upper section 134 of each blade 130 is particularly configured to facilitate the insertion of the blades into the retractor. In particular, the upper section 134 of the blade 130 is configured so that an upward extending and generally oblong shaped lip member 136 is received in the ridged slots 132 located on the bottom surface of the first and second arms, 112 and 116. This surface further includes a raised ball member 137 which slides in a further slot 139 located in the ridged slots. The ball member may be slightly depressible so that it may be slid beyond the further slot 139 so that during the initial placement of the retractor, the blades may be positioned to extend nearly linearly along each arm in an insertion position. As the arms are retracted, the inner and outermost blades move to a retraction position to assume a slightly curved shape. In the preferred form of the present invention, the retraction position generally approximates the anatomy of the patient and allows the pressure of the sternum of the patient to be evenly distributed among the blades. The use of the ball member and the further slots and the ridged slots allow the blades to temporarily assume the linear configuration and also rise slightly to provide a lower profile and maintain the retraction edge. Once the blades are inserted into the sternum, the slight release of the pressure during the insertion allows the ball member to return to the innermost end of the further slot. In the present invention, the blades preferably follow the slightly curved shape of the retraction position and provide optimum leverage to retract the sternum of the patient. The upper section 134 of the blade 130 extends generally along the bottom surface of the first and second arms, 112 and 116 and is positioned so the blade 130 extends a short distance inwardly of the front edge surfaces 120a and 120c of the arms 112 and 116. The blades 130 also include a lower section 138 which extends downwardly from the upper section 134 of the blade 130 in a curved manner to extend beneath the bottom surface of the retractor to readily engage the sternum of the patient. The lower section also preferably curves backward a short distance towards the outer edge surface 121 of the first and second arms, 112 and 116, to form a blade 130 having an overall C or L shape that facilitates the positioning and retention of the sternum of the patient adjacent thereto. Therefore, the blades 130 in conjunction with the displacement of the first and second arms result in the desired retraction of the tissue, bone etc. for the surgical procedure. Although the blades are shown as being receivable in the ridged slots 132, it is anticipated that the blades 130 of the present invention may also be received in slots or similar structures on the arms of the retractors.

The stabilization sub-system or stabilization arm 104 of the present invention preferably includes an elongate handle segment 180 that interacts with the retractor 102 and the stabilization device 106. The handle segment 180 is preferably a rigid tubular member that includes a distal connector 181 on the distal end thereof to pivotally and removably retain the stabilization device 106 thereon. The handle segment 180 is attachable to the retractor 102 by a connector such as a mounting mechanism or sled member 140. The proximal end of the handle segment 180 preferably includes a movable knob 184 and a fixed knob 186 thereon. The movable knob 184 is connected to an elongate rod that is threaded through the handle segment 180 and extends to the distal connector 181. The fixed knob 186 is fixed proximally of the movable knob 184 on the handle segment 180 to allow the user to rotate the stabilization device 106 by manipulating this fixed knob 186 when the stabilization device 106 is connected to the distal connector 181 of the handle segment 180.

As illustrated, the distal connector 181 consists of a generally bulbous member having an elongate slot 187 extending through at least one side thereof. The slot 187 is sized to allow the post member 196 of the stabilization device 106 to pass laterally therethrough to allow the stabilization device to be easily mounted on or removed from the stabilization arm 104. Additionally, the use of the bulbous shape on the post member 196 and the complementary shape of the slot 187 allows the stabilization device to be pivotal and rotatable about the handle segment to enable the surgeon to position the stabilization device 106 in the desired position and against nearly any surface of the heart of the patient. The stabilization device 106 is fixed in the desired position relative to the handle segment 180 by rotating the movable knob 184 with respect to the handle segment and/or the fixed knob so that a portion of the elongate rod moves with respect to the outer surface of the handle segment 180 and extends into the distal connector 181 to contact and engage the post member 196 of the stabilization device 104. This movement of the elongate rod with respect to the distal connector causes the post member to press against the lower lip surfaces 189 of the distal connector. The preferred, generally pear-like, shape of the distal connector 181 optimizes the connection between the distal connector 181 and the post member 196 to enable the stabilization device 106 to be selectively retained within the distal connector 181 while allowing for the pivotal and rotational movement necessary for the use of this device in a cardiac application where space is at a premium and the device must be as versatile as possible to accommodate the surgeons needs without undue experimentation.

The stabilization arm 104 of the preferred embodiment also includes a sled member 140 operatively connected thereto. The sled member 140 is configured so the surgeon has multiple axis positioning capability for the stabilization device 106 while requiring a minimum of manipulation. In an exemplary embodiment, the bottom section of the sled member 140 includes a front edge lip 150, a movable second lip 152 and an actuator lever 154. The actuator lever 154 is pivotally connected to an elongate slot in the second lip 152 by a pin 158 which is preferably offset with respect to the axis of rotation of the actuator lever 154 so that movement of the actuator lever 154 causes the second lip 152 to move towards and away from the front edge lip 150. The front edge lip 150 is configured so that the interior of this lip conforms generally to the shape and configuration of any of the retractor front edge surfaces 120*a–c*. The front edge lip 150 also includes a portion that extends backwards under the front edge surfaces 120*a–c* of the arms and/or rack segment of the retractor so the front edge lip 150 preferably forms an acutely angled surface that is easily secured at any location on any of the front edge surfaces 120*a*, 120*b* or 120*c* of the retractor 102.

As also shown in the drawings, the second lip 152 of the sled member 140 is a semicircular or oblong shaped member that is disposed in the bottom of the sled member 140 a distance back from the front edge lip to selectively engage the recessed side of any of the step surfaces 122*a–c* of the retractor. The second lip 152 also is generally configured so the inside interior surface 151 of the sled member 140 extends arcuately across and lies upon the top surface of the retractor 102 between a front edge surface 120*a–c* and the associated step surface 122*a–c* of the retractor. The second lip 152 is slidably mounted on the bottom side of the sled member 140 and is movable in response to rotation of the actuator lever 154 to form an acute step surface engaging angle between the sled second lip 152 and the inside interior surface 151 to securely retain the selected step surface 120*a*, 120*b* or 120*c* therein.

One skilled in the art would recognize that there are a number of means available in the art for removably securing the sled member 140 to the front edge surface and step surface 122*a–c* of the retractor. For example a wing nut or similar threaded type of arrangement where the wing nut would act on the vertical surface of the retractor step may be used. However, the use of the actuator lever 154 of the preferred embodiment provides the surgeon with a quick and simple means for attaching the sled member 140 to any desired location on the retractor 102 with a single handed operation of the actuator lever 154. Additionally, the distance of travel of the actuator lever 154 is chosen so as to be preferably less than about 180 degrees to further facilitate the single handed attachment of the sled member 140 to the retractor 102. Additionally, the actuator lever 154 is preferably positioned on the side of the sled member 140 which is adjacent to the outer edge surface 121*a–c* of the retractor 102 so as to not interfere. with the operative field or vision of the surgeon.

In an alternate embodiment, a cam shaped member may be located on the bottom surface of the sled member instead of the second lip 152 described above. The cam shaped member may be formed as a generally circular member that is configured with a flat region on at least one part of the circumference. To place the sled member onto the retractor of this embodiment, the actuator lever may be rotated so that cam is rotated and the flat side of the cam faces the sled front edge lip. After the sled member is placed on the retractor, the actuator lever is again rotated so the curved portion of the cam will come into contact with and engage the vertical surface of the retractor steps.

As indicated above, rotation of the cam may be accomplished by rotation of the actuator lever and the actuator lever is movable between various positions wherein the cam is fully contacting, partially contacting or spaced apart from the top surface and step of the retractor. It is within the scope of the present invention, however, for the cam to be spring loaded such that the cam automatically rotates so the curved portion of the cam contacts the retractor step when the actuator lever is not being held by the surgeon. In other words, the cam may be biased so that the curved portion of the cam faces the sled front edge lip.

It is within the scope of the present invention for the cam or second lip to have any geometric configuration or shape consistent with the preferred features of the present invention, for example, some of these preferred features relate to the ease and versatility of removably mounting the sled member 140 onto and removing the sled member from the retractor 102. For example, directly mounting and directly removing the sled without being required to slide the sled member on and off the ends of the arms of the retractor 102 as well as for providing the ability to mount the sled member 140 onto the rack segment 114 of the retractor. Furthermore, the ability to mount the sled member 140 on any one of the arms and rack segment on a temporary basis and then being able to slide the sled member into the final desired position is an advantage over the currently available retractors. This is particularly true in the preferred form of the present invention where, in the midway position of the actuator, the actuator lever will cause the retention of the sled member on the retractor while allowing sliding movement therebetween. The actuator lever may then be moved to the engaged position to lock the sled member and therefore, the stabilization arm in the desired position on the retractor.

In the preferred embodiment of the present invention, the sled member 140 also includes an upper section including a knob 160, a stabilization arm clamp 162, a sled pin clamp 166, and a threaded rod 170 therein. This portion of the sled member 140 provides the surgeon with the rotational movement of the stabilization arm 104 in a combination of horizontal and vertical directions as well as allowing for the sliding and rotational movement of the handle segment 180 therethrough, all of which are advantageously controlled by the operation of the single knob 160 that is located along the periphery of the operative field The sled pin 158 extends upwardly from the portion of the bottom section of the sled member 140 to form a first or vertical axis of rotation between the bottom section that includes the front edge lip 150, second lip 152 and the actuator lever 154 described above and the upper section described below. This arrangement enables the bottom section of the sled member to be rotatable with respect to the upper section of the sled member 140 independently of whether or not the sled member is locked into position along the arms and/or rack segment of the retractor. Additionally, this orientation places the upper section of the sled member preferably directly above the front edge of the retractor as shown. This orientation significantly increases the range of motion of the sled member and therefore the range of motion of the stabilization arm and ultimately significantly increases the versatility and range of motion of the stabilization device. For example, rotation of the sled member 140 and stabilization arm 104 will allow the user to position the stabilization device 106 beneath the arms and/or rack segment by allowing the aperture 164 which contains the handle segment 164 to extend inwardly of the front edge 120 of the retractor 102. This orientation is particularly useful in situations where the posterior surface of the heart is being operated on as well as in certain situations where the selected portion of the heart is manipulated to a side of the operative field. This type of orientation may require the handle segment to be oriented at an angle which is generally greater than perpendicular to the width dimension of the arms or rack segment. Alternately, the sled pin may be angled to cause the upper section of the sled member to extend inwardly of the front edges of the arms and rack segment to further increase the versatility of the present invention. The sled pin 158 is rotatably received in a recess or pocket 168 that is formed in left and right sections of the sled pin clamp 166 on the sled member 140. In this way, and as described hereinafter, the upper section of the sled member 140 can be rotated by the surgeon about the sled pin 158 to facilitate the rotational positioning of the stabilization arm 104 and stabilization device 106 at the desired predetermined area on the heart of the patient.

The left and right sections of the stabilization arm clamp 162 on the sled member 140 are configured so as to form a through aperture 164 therein. This aperture 164 is preferably offset from the rotational or horizontal axis of the knob 160 and threaded rod 170 to increase or decrease the angle of approach of the handle segment 180 to the operative field. As shown, the preferred configuration orients the aperture 164 above the rotational axis of the knob 160. If desired by the surgeon, the aperture 164 and therefore the handle segment 180 may be positioned below the rotational axis of the knob so that the handle segment will approach the operative field at a lower angle. The aperture 164 slidably and rotationally receives the handle segment 180 of the stabilization arm 104 therein. The stabilization arm clamp 162 is rotatably disposed about the threaded rod 170 to allow the handle segment to be rotatable about the longitudinal axis of the threaded rod 170 as well as being separately rotatable and slidable with respect to the aperture 164. The rotational surfaces between the stabilization arm clamp 162 and the sled pin clamp 166 may also preferably have a plurality of complementary ridges and valleys thereon so as to form a poker chip type surface on each of these surfaces of the clamps. The use of this type of surface preferably limits the rotational movement of the stabilization arm clamp 162 with respect to the sled pin clamp 166 when the knob 160 and threaded rod 170 are intermediately or fully tightened by providing an additional source of friction that must be overcome to rotate the handle segment with respect to the stabilization arm clamp 162. Additionally, the use of this type of surface facilitates the fine positioning of the stabilization device 106 by preventing the rotational movement of the stabilization arm clamp 162 while the surgeon is still able to overcome the frictional resistance to the rotational and sliding movement the handle segment 180 when the knob 160 is not fully tightened.

The preferred form of the present invention also includes the threaded rod 170 that is fixedly attached to the knob 160 and extends between the knob 160 and the outer section 167 of the sled pin clamp 166. In this way, and as described hereinafter, the stabilization arm clamp 162 and thus the handle segment 180 of the stabilization arm 104 can be rotated by the surgeon about the threaded rod 170 prior to the knob 160 being rotated to a fully engaged position wherein relative movement is prevented. Additionally, the handle segment 180 may also slide and/or be rotated with respect to the stabilization arm clamp 162 through the aperture 164 to facilitate positioning of the stabilization device 106 through the manipulation of an actuation member such as the single knob described herein or through a single lever or handle.

The knob 160 is secured to one end of the threaded rod 170 and the other end of the rod engages the outer section 167 of the sled pin clamp 166. The sled pin clamp 166 and the stabilization arm clamp 162 are each located rotationally about the threaded rod 170 and are compressively controlled thereby. Thus, rotation of the knob 160 in one direction (e.g., clockwise direction) moves the left and right sections of each of these clamps towards each other (i.e., compresses the clamps) so as to clamp onto each of the sled pin 158 and the handle segment 180 respectively. The compression of the sled pin 158 by the sled pin clamp 166 limits the rotational movement of the bottom section of the sled member 140 with respect to the upper section of the sled member 140 to limit the generally horizontal movement of the stabilization arm 104 with respect to the retractor 102. The compression of the handle segment 180 by the stabilization clamp 162 prevents the rotational and sliding movement of the handle segment 180 through the aperture 164 and therefore causes the stabilization device 106 to be held in a fixed position relative to the sled member 140 and the retractor 102 to limit the generally vertical movement of the stabilization arm 104 with respect to the retractor 102. Similarly, rotational movement between the stabilization arm clamp 162 and the sled pin clamp 166 is limited by tightening the knob 160 to a fally engaged position. Rotation of the knob in the opposite direction (e.g., counterclockwise direction) causes each of these clamps 162 and 166 to separate and enable the clamps to be rotatable about the sled pin 158 and/or the threaded rod 170. In the preferred form of the present invention, each of the clamps include a spring member (not shown) therein to facilitate the separation of the clamps as the knob is rotated in this position. Additionally, the handle segment 180 can slide and rotate within the stabilizer arm clamp 162 and through the aperture 164. As one skilled in the art would appreciate, the knob 160 can be rotated in the direction of clamping so as to increase the resistance of rotation about the sled pin 158 and to increase the resistance to sliding and/or rotation of the handle segment 180 in the aperture, without completely preventing such rotation and/or sliding. This may be done to facilitate the precise positioning of the stabilization device 106 by the surgeon. Additionally, the clamps 162 and 166 may be arranged so that the initial rotation of the knob 184 may first release either the sled pin 158 or the handle segment 180 prior to the release of the other of the sled pin 158 or handle segment 180. Additionally, the clamps 162 and 166 may be arranged to initially allow for or prevent the rotation of the stabilization arm clamp 162 relative to the sled pin clamp 166. Thereafter, the clamps 162 or 166 may release the sled pin 158 and handle segment 180 at the same time or sequentially. Although the preferred form of the present invention is described herein as a knob, it is anticipated that a lever or similar actuation member may be used to accomplish the desired, orientation of the stabilization device 106 relative to the retractor 102.

In an alternate embodiment of the present invention, the bottom surface of each of the first and second arms, 112 and 116, on the retractor 102 include removable sternal blades 210 attached thereto. Each blade 210 is removable so as to facilitate the use of the retractor in a full or mini-sternotomy procedure by allowing for the selective positioning and spacing of the blades 210 as desired for the particular procedure as well as for increasing the ease of use of the retractor 102 and blades 210. As illustrated, the blades 210 of this embodiment are positioned along the bottom surface of the arms 112 and 116 and are preferably formed to include one or more downwardly extending blade elements 220 which are attached to the base sections on each arm of the retractor. As with the prior embodiment, the blades are preferably slightly pivotal in the horizontal and vertical directions with respect to the arms. For example, the blades 210 may preferably pivot up to about thirty degrees in the horizontal direction and slightly or not at all in the vertical direction. The blades 210 are slidable into elongate ridged slots 132 on the bottom surface of the first and second arms, 112 and 116. The blades 210 may also swivel a limited distance and are selectively positioned in the slots 132 so as to evenly distribute the retraction forces or pressure along the contour of the sternum of the patient. An upper or base section 212 of each blade 210 is particularly configured to facilitate the insertion of the blades into the retractor. In particular, the upper surface 214 of the base section 212 of the blade 210 is configured so that an upward extending and generally oblong shaped lip member 216 is received in the ridged slots 132 located on the bottom surface of the first and second arms, 112 and 116. This upper surface 214 further includes a raised ball member 218 which slides in a further slot 139 located in the ridged slots. The ball member 218 may be slightly depressible so that it may be slid beyond the further slot 139 so that during the initial placement of the retractor, the blades 210 may be positioned to extend nearly linearly along each arm in an insertion position. The use of the ball member and the ridged slots allow the blades to temporarily assume the linear configuration and also rise slightly to provide a lower profile and maintain the retraction edge.

Figure 14:
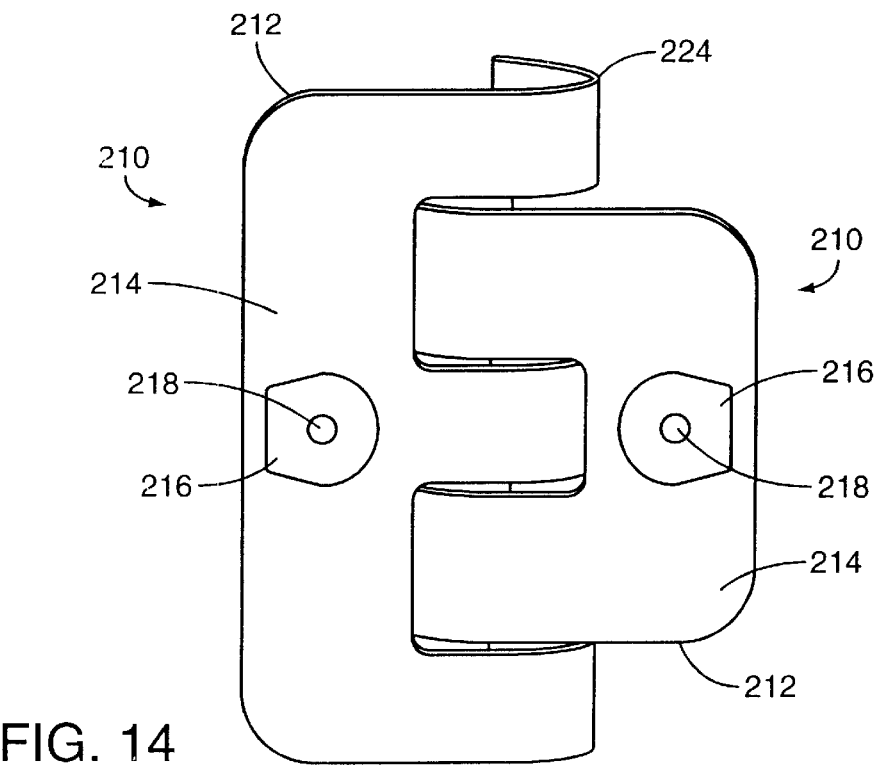
FIG. 14 is a top perspective view of an alternate form of the blade members of the present invention.
Figure 15:
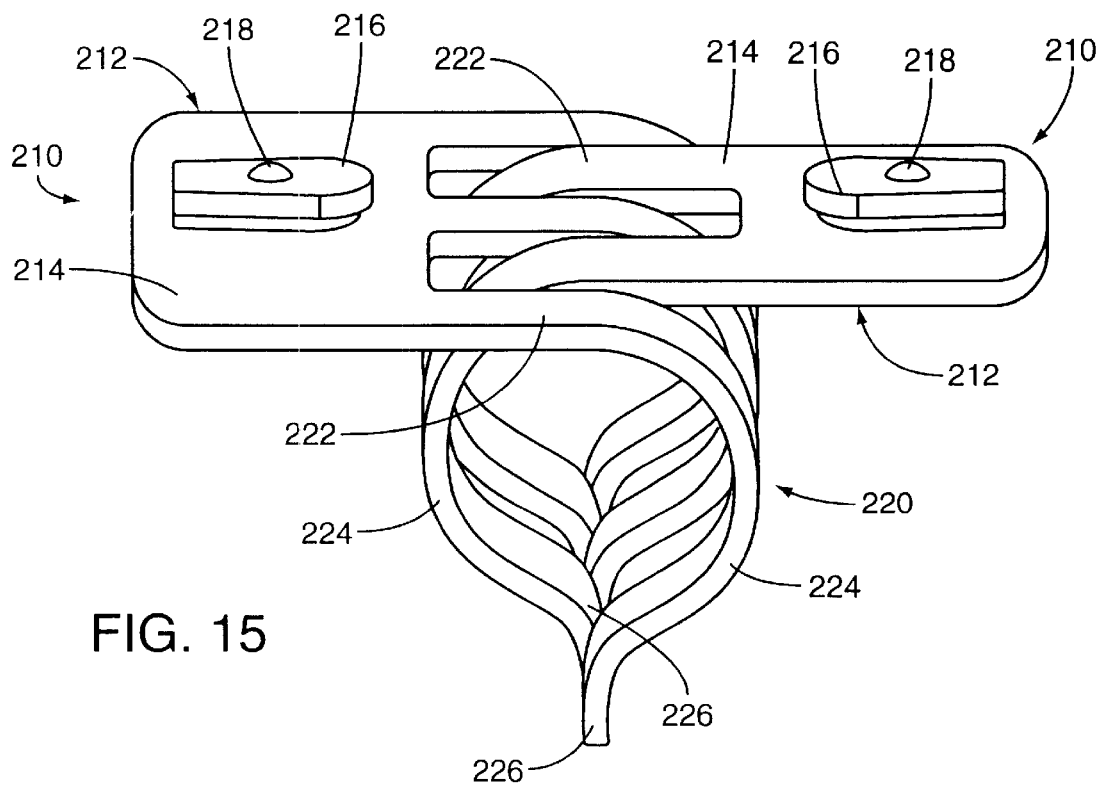
FIG. 15 is a top elevated perspective view of the alternate form of the blade members of the present invention shown in FIG. 14.

As shown in FIGS. 14–16, the base section 212 of the blades 210 of this embodiment may include one or more blade elements 220 that extend inwardly and downwardly from the base section 212. As described, the base sections 212 preferably include a single oblong lip member 216 on the upper surface 214 thereof and two or three blade elements 220 extending inwardly and downwardly therefrom. Additionally, the blade elements 220 are preferably configured to provide a nested, alternating or interlocking arrangement when the arms of the retractor are in the closed position. The blade elements 220 preferably include a first section 222 that extends inwardly from the base section 212. As shown, the blade elements 220 on the first section 222 preferably nest with the complementary blade elements of the first section from the blade 210 on the opposite arm of the retractor. The second section 224 of the blade elements 220 are preferably inwardly and downwardly curved at an angle of about 180 degrees. The second section 224 of the blade elements 220 extend downwardly from the first section 222 beginning at the approximate midpoint of the inner surface of the arms of the retractor. The third section 226 of the blade elements 226 are preferably straight and extend downwardly from the second section 224 and provide a gradual transition between the straight third section and the curved second section. As shown, the third section 226 is preferably aligned with the inner surface of the arms of the retractor when the arms are in the closed position.

The surgeon initially makes a long incision down the middle of the chest, saws through the sternum, spreads the two halves of the sternum apart using the blades 210 of the surgical retractor. Initially, the arms of the retractor are in the closed position so the blades 210 are in the nested orientation wherein the blade elements 220 on each arm are generally linearly aligned. The surgeon initially places the third section of the blades into the incision. The surgeon then begins spreading the arms while pressing down on the retractor, this motion causes the tissue of the patient to contact and engage the second section of the blades so that the tissue is received along the inner surface of the curved portion of the second section of the blade elements. Additionally, as the blade elements 220 are inserted into the sternum, the slight release of the pressure during the insertion allows the ball member 218 to return to the innermost end of the further slot and the blade elements 220 may pivot slightly in the vertical and horizontal directions so that the blades 210 provide optimum leverage to retract the sternum of the patient. As the distance between the arms is increased, the curvature of the second section 224 engages and retains the tissue along the sternum of the patient to provide secure and stable retraction of the sternum of the patient.

The use of the stabilization system 100 according to the preferred aspect of the present invention can be best understood from the following discussion with reference to the drawings. Although the following discussion makes reference to the use of the stabilization system specifically in connection with a coronary artery bypass grafting a-surgical procedure, the use of the stabilization system of the present invention is not limited to such uses.

After appropriately preparing and positioning the patient for the surgical procedure and completing those actions required in advance of the use of the stabilization system, the arms 112 and 116 of the retractor 102 would be closed such that the upper portion 134 of the blades 130 or the third section 226 of the blades 210 are generally abutting each other. The surgeon then positions the lower sections 138 or third sections 226 of each of the blades adjacent to the incision and pushes down on the retractor or otherwise manipulates the blades and the patient so the blades are pushed through the incision and past the sternum as described above. Thereafter, as the arms of the retractor are separated, the blade elements pull the chest of the patient open to provide the desired surgical area.

After inserting the retractor, the surgeon displaces the two retractor arm segments 112,116 with respect to each other by rotating the handle 118 on the second arm segment 116. As the surgeon opens the sternum of the patient, they also release any underlying connective tissue and open the pericardium surrounding the heart of the patient. In order to provide for visualization of the heart, the pericardium that surrounds the heart is retracted by placing sutures (not shown) through the pericardium and then threading the sutures through the slots 123 on the retractor arms to ensure that the sutures are spaced apart from the operative field. As mentioned above, the clamps (not shown) holding the sutures may then be positioned in the slots so that the distal end of the clamping instrument is positioned in the through holes 124. This allows the sutures and clamps to be positioned out of the way of the surgeon for the subsequent procedure. After performing any subsequent actions to further open the sternum of the patient to create the desired field of view and assess the viability of the heart to perform the bypass grafting procedure on one or more vessels, the surgeon mounts the stabilization arm 104 onto one of the retractor arm segments 112,116 or the rack segment 114 in the position that they anticipate will provide the best access while minimizing the obstruction of their view for the particular procedure.

It should be recognized that the bypass grafting procedure may involve the arteries or branches thereof on nearly any surface of the heart including the posterior or backside of the heart. Therefore, having the capability to mount the stabilization arm to the rack segment 114 or either of the arms, 112 or 116, of the retractor can be particularly advantageous. With the preferred form of the present invention, the stabilization arm 104 may be positioned near the top of the operative field on the rack segment 114 rather than only along the sides of the operative field. The retractor 102 is typically arranged on the body so the throat of the retractor faces the head of the patient and the surgeon is typically located on one side of the patient while a nurse is located on the other side of the patient and instruments are passed across the body of the patient throughout the procedure. Therefore, with the preferred form of the present invention, the surgeon has an additional surface to choose from when they are deciding which surface will provide the best access to the desired surface of the heart while not interfering with the procedure.

To mount the stabilization arm 104 onto the retractor 102, the surgeon rotates the sled actuator lever 154 so the second lip 152 is in a disengaged position and is spaced from the front edge lip 150 of the sled member 140. After so configuring the sled member 140, the surgeon positions the sled member 140 on the retractor 102 at any of a number of available positions on the arms, 112 and 116, or the rack segment 114 by positioning the front edge lip 150 over the front edge of the selected arm or rack segment. With the preferred configuration of the sled member 140, the surgeon need not slide the sled member along the entire length of a retractor arm or be required to select from a limited number of predetermined positions, but can place the sled member 140 directly at the desired position. In this way, a surgeon can removably position the sled member 140 anywhere on the rack segment 114 or the arms 112, 116 of the retractor 102 without having to first assemble the retractor with a sled member 140 initially positioned in any of these predefined areas. An advantage of this configuration is that the surgeon may initially position the sled member 140 in a position that they anticipate will be close to where they will ultimately want it. If during the procedure, a different location is needed or provides better access, the surgeon may either slide the sled member 140 along the previously selected arm or rack segment to the desired location or they may remove the sled member 140 from the retractor and try various locations to see which location on the arms and rack segment provides the best access for the particular procedure. In addition, such a sled configuration also allows the surgeon to perform certain surgical procedures without having to worry about the sled member 140 cutting or interfering with any sutures that may be passing over the retractor while positioning the sled member 140. Furthermore, if multiple blood vessels are operated on or access to multiple surfaces is desired, the orientation of the sled member may be readily adjusted to accommodate the needs of the particular part of the procedure.

The surgeon may next fix the sled member in place by positioning the front edge lip 150 of the sled member 140 over the front edge surface 120a, 120b or 120c on the desired area of the retractor 102 and then rotating the sled actuator lever 154 partially or fully, as desired, so the second lip 152 contacts and engages the vertical extending surface of the corresponding step surface 122a–c on the retractor 102. One surgeon has placed the sled member on the retractor, they may then initially position the stabilization device 106 near the ultimate desired location along the surface of the heart by loosening the movable knob 184 and rotating the fixed knob 186 as well as loosening the knob 160 on the sled member to orient the stabilization device 106 and stabilization arm 104 in the tentative desired position. It should be recognized that this process may be repeated as often and whenever necessary to modify the position of the stabilization device 106 at the desired location or area of the heart.

Thereafter, the surgeon may loosen knob 160 and rotate the top section of the sled member 140 about the sled pin 158 and also move the handle segment 180 lengthwise and/or rotationally with respect to the sled member 140 to position the handle segment within the stabilization arm 162 clamp through aperture 164 so as to position the stabilization device 106 with respect to the predetermined area of the heart to be stabilized. Once the surgeon is satisfied with the location of the stabilization device 106 on the heart of the patient, the surgeon may tighten knobs 160 and 184 to ensure that the stabilization arm 104 and stabilization device 106 are retained in the desired position throughout the remainder of the procedure. Once the stabilization device 106 is in the desired contacting relationship with the predetermined area of the heart, the surgeon may tighten the knob 160 of the stabilization arm 140 so as to prevent further rotation about the threaded rod and the sled pin and also to prevent sliding of the handle segment in the aperture. The surgeon may also tighten the knob 184 of the handle segment 180 so as to tighten the connection between the distal connector 181 on the handle segment and the post member 196 on the stabilization device 106 prevent further motion of the stabilization device 106 about the end of the stabilization arm 104.

After completing the grafting procedure, the surgeon may then remove the stabilization arm 104 and stabilization device 106 by essentially reversing the above described steps or the surgeon may simply release the actuator lever 154 and remove the entire stabilization arm and stabilization device from the operative field. Similarly, the actuator lever may be moved to a position between the engaged and disengaged positions so that the stabilization arm may be moved out of the way while a subsequent procedure is performed or to attach a new stabilization device thereon.

In the foregoing discussion, the stabilization system of the present invention is described in terms of clamping and supporting a stabilization device. It is within the scope of the present invention, however, for the system to be configured to removably secure any of a number of surgical instrumentalities to the retractor such as for example diaphragm or valve retractors. Additionally, although one stabilization arm is described as being in use at a time, it is within the scope of the present invention for plurality or a multiplicity of stabilization arms to be secured to the retractor. For example, one stabilization arm could be provided to support a diaphragm retractor and another stabilization arm provided to support a tissue stabilizer or suction device. Furthermore, the blade elements described above may be attached to the retractor arms using a variety of attachment configurations and may include one or more blade elements extending therefrom that are arranged in a variety of configurations that may be used to assist in the retraction of the chest or similar tissue of the patient.

Although a preferred embodiment of the invention has been described using specific terms, such description is for illustrative purposes only, and it is to be understood that changes and variations may be made without departing from the spirit or scope of the following claims.

What is claimed is:

1. A system for use in a surgical procedure, comprising:
a retractor having a plurality of retractor arms thereon and a segment interconnecting said retractor arms wherein said retractor arms are movable with respect to each other and include top and bottom surfaces thereon wherein said bottom surface of each of said arms includes a plurality of elongate slots having a blade engaging surface on said bottom surface of said arms; and
a plurality of blades each having an upper surface with a raised surface thereon and said upper surface of said blades being sized to be slidably contacting with said blade engaging surface of said slot to allow horizontal movement therebetween and said blades further having at least one downwardly extending blade element thereon.

2. The system of claim 1 wherein each of said plurality of blades are slidable into one of said slots and said blades are spaced apart from said top surface of said arms.

3. The system of claim 1 wherein at least one of said blades include a third section thereon that is curved relative to first and section sections thereof.

4. The system of claim 3 wherein said first section of said at least one of said blades is oriented generally perpendicular to said third section of said blade element.

5. The system of claim 3 wherein said first section of said at least one of said blades is oriented generally parallel to said top surface of at least one of said retractor arms of said retractor.

6. The system of claim 3 wherein each of said retractor arms include inner surfaces and said third section of said at least one of said blades is generally aligned with the inner surface of the retractor arms.

7. The system of claim 6 wherein said second section of said at least one of said blades includes an inner and outer surface and said second section extends outwardly beyond the inner surface of at least one of the retractor arms.

8. The system of claim 3 wherein second section of said at least one of said blades has an angle of curvature of approximately 180 degrees.

9. A system for use in a surgical procedure, comprising:
a retractor having a plurality of retractor arms thereon and a segment interconnecting said retractor arms wherein said retractor arms are movable with respect to each other and include top and bottom surfaces thereon wherein said bottom surface includes a blade engaging surface on said bottom surface of said arms;
a plurality of blades each having an upper surface with a raised surface thereon and said upper surface of said blades being sized to be slidably contacting with said blade engaging surface to allow horizontal movement therebetween and said blades further having at least one downwardly extending blade element thereon; and
wherein said blade engaging surface on said bottom surface of said arms include a plurality of ridged slots and a plurality of further slots are located in said ridged slots and said blades further include a raised member thereon which is sized to be in slidable contact with said further slots.

10. The system of claim 9 wherein said raised member includes a ball member that extends upwardly with respect to said upper surface of each of said blades.

11. A blade member for use on surgical retractors, said blade member including:
a body section having an upper surface and said upper surface of said body section having a member thereon that is sized to slidably contact an arm of a surgical retractor and said member is depressible relative to said upper surface of said body section upon contact with an arm of a surgical retractor; and
a blade element extending from said body section and said blade element having a first section and a second section wherein the second section is curved relative to the first section and said second section extends downwardly therefrom.

12. The blade member of claim 11 wherein said member includes a ball member associated therewith.

13. The blade member of claim 11 wherein said body section includes a lip member extending along the periphery thereof.

14. The blade member of claim 11 wherein said body section generally includes an oblong member having a lip surface extending along the periphery thereof.

15. The blade member of claim 11 wherein said blade element further includes a third section extending generally downwardly from said second section and said third section is oriented generally perpendicular to said first section.

16. The blade member of claim 15 wherein said second section includes an angle of curvature of about 180 degrees.

17. The blade member of claim 11 wherein said body section includes at least two spaced apart blade elements extending downwardly therefrom and said blade elements are configured relative to each other to align with blade elements from an additional blade member.

18. The blade member of claim 11 wherein said first section is generally aligned with said body section and said second section curves downwardly relative to said first section.

19. A system for use in a surgical procedure, comprising:
a retractor having a plurality of retractor arms thereon and a segment interconnecting said retractor arms wherein said retractor arms are movable with respect to each other and top and bottom surfaces thereon wherein said bottom surface includes a plurality of ridged slots on said bottom surface of said arms; and
a plurality of blades at least one of which has an upper surface with a raised surface thereon and said upper surface of said at least one of said blades being sized to be in slidable contact with at least one of said ridged slots to allow horizontal movement therebetween and said at least one of said blades further having at least one downwardly extending blade element thereon;
a ball member that extends upwardly with respect to said raised member;
a blade element associated with said upper surface of said at least one of said blades and said blade element including a first section that is oriented generally parallel to at least one of the arms of the retractor;
a second section on said blade element wherein said second section includes a downward curve extending from said first section;
a third section on said blade element wherein said third section extends downwardly from said second section and is oriented generally perpendicularly to said first section; and
wherein each of said retractor arms include inner surfaces and said third section of said blade elements are generally aligned with the inner surface of at least one of the retractor arms and said second section extends beyond said inner surface of at least one of said retractor arms.

* * * * *